United States Patent
von Sprecher et al.

[11] Patent Number: 5,145,868
[45] Date of Patent: Sep. 8, 1992

[54] ALKANOPHENONES USEFUL FOR TREATING ALLERGIES

[75] Inventors: Andreas von Sprecher, Oberwil, Switzerland; Andreas Beck, Freiburg, Fed. Rep. of Germany

[73] Assignee: Ciba-Geigy Corporation, Ardsley, N.Y.

[21] Appl. No.: 794,608

[22] Filed: Nov. 15, 1991

Related U.S. Application Data

[63] Continuation of Ser. No. 583,783, Sep. 14, 1990, abandoned.

Foreign Application Priority Data

Sep. 19, 1989 [CH] Switzerland ............ 3401/89

[51] Int. Cl.$^5$ .......... A61K 31/35; A61K 31/41; C07D 311/24; C07D 257/04
[52] U.S. Cl. .......... 514/456; 549/402; 549/60; 548/525; 548/253; 514/444; 514/422; 514/382
[58] Field of Search .......... 549/402, 60; 548/525, 548/253; 514/456, 444, 422, 382

[56] References Cited

U.S. PATENT DOCUMENTS

| | | | |
|---|---|---|---|
| 4,474,788 | 10/1984 | Bantick | 549/402 |
| 4,609,744 | 9/1986 | Young et al. | 549/402 |
| 4,649,215 | 3/1987 | Von Sprecher et al. | 360/152 |
| 4,761,425 | 8/1988 | Girard et al. | 514/456 |
| 4,785,004 | 11/1988 | Von Sprecher et al. | 514/311 |
| 4,808,572 | 2/1989 | Beck et al. | 514/18 |

FOREIGN PATENT DOCUMENTS

| | | |
|---|---|---|
| 0123543 | 10/1984 | European Pat. Off. |
| 134111 | 3/1985 | European Pat. Off. |
| 147217 | 7/1985 | European Pat. Off. |
| 206741 | 12/1986 | European Pat. Off. |
| 228045 | 7/1987 | European Pat. Off. |

Primary Examiner—Nicky Chan
Attorney, Agent, or Firm—Irving M. Fishman; Karen G. Kaiser

[57] ABSTRACT

Substituted alkanophenones of the general formula

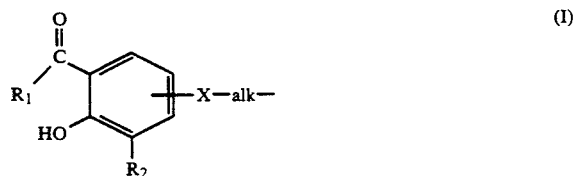

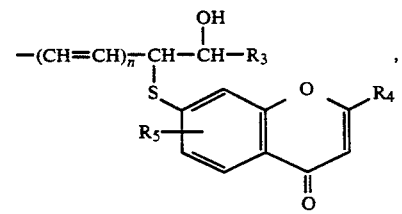

in which $R_1$ is unsubstituted or fluorinated lower alkyl, $R_2$ is hydrogen, or unsubstituted or fluorinated lower alkyl or lower alkenyl, X is lower alkylene, oxy, thio or a direct bond, alk is lower alkylene, n is 1 or 2, $R_3$ is a 5-membered heteroaryl radical that contains 1N, O or S atom as hetero atom and is unsubstituted or is substituted by unsubstituted or fluorinated lower alkyl, by etherified or esterified hydroxy, by unsubstituted or lower alkylated amino and/or by free, esterfied or amidated carboxy, $R_4$ is free, esterified or amidated carboxy or 5-tetrazolyl, and $R_5$ is hydrogen or lower alkyl, have leucotriene-antagonistic properties can e used as antiallergic active ingredients in medicaments.

20 Claims, No Drawings

ALKANOPHENONES USEFUL FOR TREATING ALLERGIES

This application is a continuation of application Ser. No. 583,783, filed Sep. 14, 1990, now abandoned.

The invention relates to novel substituted alkanophenones of the general formula I

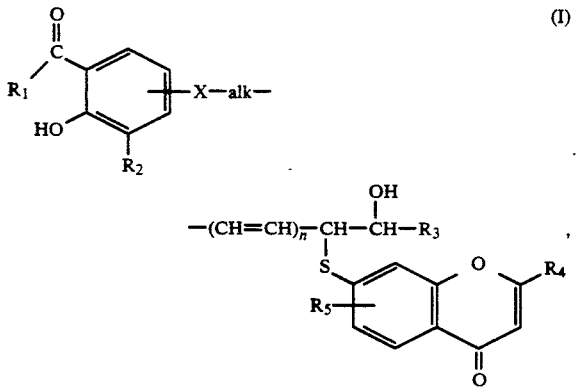

in which $R_1$ is unsubstituted or fluorinated lower alkyl, $R_2$ is hydrogen, or unsubstituted or fluorinated lower alkyl or lower alkenyl, X is lower alkylene, oxy, thio or a direct bond, alk is lower alkylene, n is 1 or 2, $R_3$ is a 5-membered heteroaryl radical that contains 1N, O or S atom as hetero atom and is unsubstituted or is substituted by unsubstituted or fluorinated lower alkyl, by etherified or esterified hydroxy, by unsubstituted or lower alkylated amino and/or by free, esterified or amidated carboxy, $R_4$ is free, esterified or amidated carboxy or 5-tetrazolyl, and $R_5$ is hydrogen or lower alkyl, and their salts, to processes for their preparation, to pharmaceutical preparations containing them as active ingredient, and to their use as active ingredients in medicaments.

The spatial arrangement shown in the above formula I for the preferred compounds in which the O atom of the hydroxy group is in the relative trans-configuration with the S atom is to be understood as follows: the symbols in the first line lie above the plane of the drawing and the symbols in the third line therefore lie below the plane of the drawing (or vice versa), which for the formula shown corresponds to the opposite configuration, (RS)—(SR), according to the Kahn-Ingold-Prelog convention at the carbon atom bonded to the sulfur atom, (C—S—), and the carbon atom carrying the hydroxy group, (C—OH). When n is 2, the enantiomers having the S(C—S—), R(C—OH)-configuration and, when n is 1, the enantiomers having the R(C—S—), S(C—OH)-configuration are especially preferred. In a vinylene or buta-1,3-dienylene radical represented by the symbol —(CH=CH)$_n$, the double bond or the double bond of the butadienylene radical originating from the carbon atom bonded to the radical alk is preferably, but not necessarily, in the cis-configuration, usually designated (Z), the other double bond then preferably, but again not necessarily, having the trans-configuration, usually designated (E).

Unsubstituted or fluorinated lower alkyl is lower alkyl or mono-, di- or poly-fluoro-lower alkyl.

Etherified or esterified hydroxy is, for example, lower alkoxy or halogen, respectively.

Unsubstituted or lower alkylated amino is, for example, amino, lower alkylamino or especially di-lower alkylamino.

5-Membered heteroaryl radicals that contain 1N, O or S atom and are unsubstituted or are substituted as indicated are, for example, pyrryl, such as 2-pyrryl, thienyl, such as 2-thienyl, or furyl, such as 2-furyl, radicals that are unsubstituted or are substituted as indicated.

Free, esterified or amidated carboxy is carboxy, esterified carboxy, such as lower alkoxycarbonyl, or amidated carboxy, such as carbamoyl or N-mono- or N,N-di-lower alkylcarbamoyl or, as $R_3$, N-(benzenesulfonyl)-carbamoyl that is unsubstituted or substituted, preferably in the phenyl moiety, by lower alkyl, lower alkoxy and/or by halogen. N-(benzenesulfonyl)-carbamoyl that is unsubstituted or substituted in the phenyl moiety as indicated is, for example, unsubstituted or monosubstituted, preferably in the ortho-position. As a free, esterified or amidated carboxy substituent of $R_3$, carboxy is especially preferred, and as $R_4$ esterified carboxy, especially lower alkoxycarbonyl, is especially preferred.

Hereinbefore and hereinafter "lower" radicals and compounds are to be understood as being, for example, those radicals and compounds containing no more than 7 and, unless otherwise indicated, preferably no more than 4 carbon atoms (C atoms).

Lower alkyl is, for example, $C_1$–$C_7$alkyl, especially straight-chain $C_1$–$C_4$alkyl, such as methyl, ethyl, propyl, isopropyl, butyl or sec.-butyl, but may also be a branched-chain $C_1$–$C_4$alkyl, such as isobutyl or tert.-butyl, or a pentyl, hexyl or heptyl radical. Lower alkyl $R_1$–$R_5$ and as a substituent of phenyl or N-(benzenesulfonyl)-carbamoyl is preferably $C_1$–$C_4$alkyl, for example methyl; lower alkyl $R_2$ is preferably $C_2$–$C_5$alkyl, for example propyl, and lower alkyl $R_3$ is preferably $C_3$–$C_7$alkyl, for example propyl, butyl or pentyl.

Mono-, di- or poly-fluoro-lower alkyl has, for example, up to and including 5 fluorine atoms and is, for example, mono-, di- or tri-fluoro-$C_1$–$C_7$alkyl, especially ω-fluoro- or ω, ω, ω-trifluoro-$C_1$–$C_4$alkyl, such as trifluoromethyl, 2,2,2-trifluoroethyl or 3,3,3-trifluoropropyl. Fluorinated lower alkyl $R_1$ and as a substituent of phenyl $R_3$ is especially trifluoromethyl, and fluorinated lower alkyl $R_3$ is preferably ω, ω, ω-trifluoro-$C_2$–$C_4$-alkyl, for example 3,3,3-trifluoropropyl.

Lower alkenyl $R_2$ is, for example, $C_2$–$C_4$alkenyl, such as vinyl, prop-1-enyl or especially prop-2-enyl (allyl).

Lower alkylene is, for example, straight-chain $C_1$–$C_7$alkylene, and in the case of X especially $C_1$–$C_3$alkylene, such as methylene or ethylene, and in the case of alk especially $C_2$–$C_6$alkylene, such as ethylene, 1,3-propylene, 1,4-butylene, also 1,5-pentylene or 1,6-hexylene.

Lower alkoxy is, for example, $C_1$–$C_4$alkoxy, such as methoxy.

Lower alkoxycarbonyl is, for example, $C_1$–$C_4$alkoxycarbonyl, such as methoxy-, ethoxy-, propoxy- or butoxy-carbonyl.

Lower alkylamino is, for example, $C_1$–$C_4$alkylamino, such as methyl-, ethyl-, propyl- or isopropyl-amino.

Di-lower alkylamino is, for example, di-$C_1$–$C_4$alkylamino, such as dimethylamino, diethylamino or N-ethyl-N-methylamino.

N-mono- or N,N-di-lower alkylcarbamoyl is, for example, N- $C_1$–$C_4$alkyl- or N,N-di-$C_1$–$C_4$alkyl-carbamoyl, such as N- methyl-, N-ethyl- or N,N-dimethyl-carbamoyl.

Halogen is, for example, halogen having an atomic number of up to and including 35, such as fluorine, chlorine or bromine. Most of the compounds of formula I can, depending upon their individual character, also be in the form of salts. Those compounds which have sufficient acidity, such as, especially, those having carboxy, tetrazolyl or sulfamoyl groups, can form salts with bases, such as, especially, inorganic bases, preferably physiologically tolerable alkali metal salts, especially sodium and potassium salts. However, ammonium salts with ammonia or physiologically tolerable organic amines, such as mono-, di- or tri-lower alkylamines, for example diethylamine, mono-, di- or tri-(hydroxyalkyl)-amines, such as tris(hydroxymethyl)-methylamine, or D-glucosamine, also come into consideration.

The compounds of formula I and their salts exhibit advantageous pharmacological properties, especially a pronounced leucotriene-antagonism.

For example, in vitro in a concentration range of approximately from 0.001 to 1.0 μmole/l, they inhibit the contraction of a smooth muscle induced by leucotriene-$D_4$(LTD$_4$). This so-called LTD$_4$-antagonism is detected experimentally, for example, as follows: in segments that have been removed from the ileum of a guinea pig weighing 300–400 g and that have been incubated in an organ bath in Tyrode's solution at 38° C. and while being gassed with a mixture of 95% oxygen and 5% carbon dioxide at a load of 1 g, contractions are induced with synthetic leucotriene D$_4$ (in potassium salt form) and are registered isotonically. The extent of the inhibition by the test compound is detected after a preliminary incubation of 2 minutes and is evaluated as IC$_{50}$, that is to say that concentration which reduces the test contraction by 50%. The compounds of formula I also have excellent activity in vivo. In addition, they have the specific and therapeutically very significant advantage of a relatively long duration of action. For example, in a standard in vivo bronchoconstriction test on guinea pigs, with aerosol administration of a solution containing from 0.001 to 1% by weight of the test compound, a marked LTD$_4$-antagonistic effect was demonstrated.

Surprisingly, many compounds of formula I also exert a pronounced inhibitory action on other physiologically important enzyme systems. For example, the inhibition of phospholipase A$_2$ obtained from human leucocytes was observed in the tested concentration range of approximately 0.5–50 μmol/l. Likewise, the inhibition of phospholipase C obtained from human thrombocytes was observed in the tested concentration range of approximately 1–1000 μmol/l. Owing to these valuable pharmacological properties, the compounds of formula I according to the invention can be used therapeutically in all cases where the action of leucotrienes results in pathological conditions, and alleviate or eliminate these conditions. Accordingly, they can be used, for example, for the treatment of allergic conditions and diseases, such as, especially, asthma, but also hay fever and obstructive pulmonary diseases, including cystic fibrosis. Owing to their anti-inflammatory activity, they are also suitable as inflammation-inhibiting agents, especially as external (topical) skin phlogistatics for the treatment of inflammatory dermatoses of any origin, as in mild skin irritations, contact dermatitis, exanthemas and burns, and also as mucous membrane phlogistatics for the treatment of inflammation of the mucosa, for example of the eyes, nose, lips, mouth and genital or anal region. They can also be used as sun screens. The marked inhibitory effect on various blood factors also points to the possibility of the therapeutic use of the compounds of formula I where thrombosis and blood coagulation are indicated.

The invention relates especially to compounds of formula I in which $R_1$ is lower alkyl or mono-, di- or poly-fluoro-lower alkyl, $R_2$ is hydrogen, lower alkyl, lower alkenyl or mono-, di- or poly-fluoro-lower alkyl, X is lower alkylene, oxy or thio, alk is lower alkylene, $R_3$ is pyrryl, thienyl or furyl each of which is unsubstituted or is substituted by lower alkyl, lower alkoxy, halogen, carboxy, lower alkoxycarbonyl, amino, N-mono- or N,N-di-lower alkylamino, carbamoyl, N-mono- or N,N-di-lower alkylcarbamoyl and/or by trifluoromethyl, $R_4$ is carboxy, lower alkoxycarbonyl, 5-tetrazolyl, carbamoyl, N-mono- or N,N-di-lower alkylcarbamoyl, or N-(benzenesulfonyl)-carbamoyl that is unsubstituted or substituted in the phenyl moiety by lower alkyl, lower alkoxy, halogen and/or by trifluoromethyl, and $R_5$ is hydrogen or lower alkyl, and to their salts, especially pharmaceutically acceptable salts.

The invention relates preferably to those compounds in which the group X is bonded in the para-position to the $R_1$—C(=O) group, that is to say compounds of formula Ia

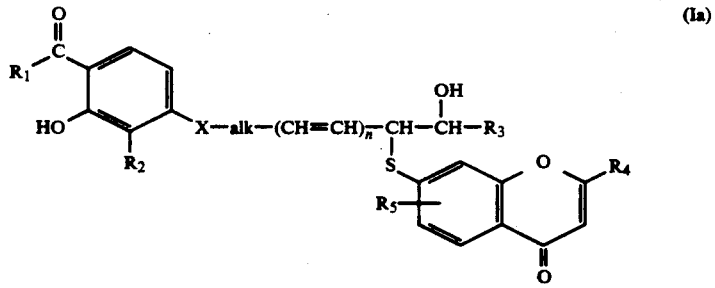

(Ia)

in which $R_1$, $R_2$, X, alk, n, $R_3$, $R_4$ and $R_5$ are as defined above, and to their salts, especially pharmaceutically acceptable salts.

The invention relates more especially to compounds of formula I and Ia in which $R_1$ is $C_1$–$C_4$alkyl, such as methyl, or ω,ω,ω-trifluoro-$C_1$–$C_4$alkyl, such as trifluoromethyl, $R_2$ is $C_1$–$C_4$alkyl, such as propyl, $C_2$–$C_4$alkenyl, such as allyl, ω,ω,ω-trifluoro-$C_1$–$C_4$alkyl, such as 3,3,3-trifluoropropyl, or, less preferably, hydrogen, X is $C_1$–$C_3$alkylene, such as methylene, oxy or thio, alk is straight-chain $C_2$–$C_6$alkylene, such as ethylene, 1,3-propylene or 1,4-butylene, n is 1 or 2, $R_3$ is pyrryl, such as 2-pyrryl, thienyl, such as 2-thienyl, or furyl, such as 2-furyl, each of which is unsubstituted or is substituted by $C_1$–$C_4$alkyl, such as methyl, $C_1$–$C_4$alkoxy, such as methoxy, halogen having an atomic number of up to and including 35, such as chlorine or bromine, trifluoromethyl, carboxy and/or by $C_1$-$C_4$-alkoxycarbonyl, such as methoxycarbonyl, $R_4$ is carboxy or N-(benzenesulfonyl)carbamoyl, and $R_5$ is hydrogen, and when n is 1, the chain carbon atom bonded to the sulfur atom preferably has the (R)-configuration and the chain carbon atom bonded to the hydroxy group preferably has the (S)-configuration or, when n is 2, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be present is preferably in the trans-configuration, and preferably to those compounds in which $R_1$ is $C_1$-$C_4$alkyl and $R_2$, X, $R_3$, $R_4$ and $R_5$ are as defined above and to their salts, especially pharmaceutically acceptable salts.

The invention relates especially, on the one hand, to compounds of formula Ia in which $R_1$ is $C_1$-$C_4$alkyl, such as methyl, $R_2$ is $C_1$-$C_4$alkyl, such as propyl, X is oxy, alk is $C_2$-$C_6$alkylene, such as ethylene, 1,3-propylene or 1,4-butylene, n is 1 or preferably 2, $R_3$ is pyrryl, such as 2-pyrryl, or especially thienyl, such as 2-thienyl, or furyl, such as 2-furyl, each of which is unsubstituted or is substituted, especially in the 4-position, by $C_1$-$C_4$-alkyl, such as methyl, $C_1$-$C_4$alkoxy, such as methoxy, halogen having an atomic number of up to and including 35, such as chlorine, trifluoromethyl or by $C_1$-$C_4$alkoxycarbonyl, such as methoxycarbonyl, $R_4$ is carboxy, and $R_5$ is hydrogen, and when n is 1, the chain carbon atom bonded to the sulfur atom preferably has the (R)-configuration and the chain carbon atom bonded to the hydroxy group preferably has the (S)-configuration or, when n is 2, the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be present is preferably in the trans-configuration, and to their salts, especially pharmaceutically acceptable salts.

The invention relates especially, on the other hand, to compounds of formula Ia in which $R_1$ is $C_1$-$C_4$alkyl, such as methyl, $R_2$ is $C_1$-$C_4$alkyl, such as propyl, X is oxy, alk is $C_2$-$C_6$alkylene, such as ethylene, 1,3-propylene or 1,4-butylene n is 2, $R_3$ is thienyl, such as 3-thienyl, or furyl, such as 3-furyl, each of which is unsubstituted or is mono- or di-substituted, especially in the 2- and/or 5-position, by $C_1$-$C_4$alkyl, such as methyl, $C_1$-$C_4$alkoxy, such as methoxy, halogen having an atomic number of up to and including 35, such as chlorine, and/or by trifluoromethyl, $R_4$ is carboxy, and $R_5$ is hydrogen, and the chain carbon atom bonded to the sulfur atom preferably has the (S)-configuration and the chain carbon atom carrying the hydroxy group preferably has the (R)-configuration and the double bond joined to the radical alk is preferably in the cis-configuration and the additional double bond which may be 60 present is preferably in the trans-configuration, and to their salts, especially pharmaceutically acceptable salts.

The invention relates more especially to compounds of formula Ia in which $R_1$ is $C_1$-$C_4$alkyl, such as methyl, $R_2$ is $C_1$-$C_4$alkyl, such as propyl, X is oxy, alk is $C_2$-$C_5$alkylene, such as ethylene, 1,3-propylene or 1,4-butylene, n is 2, $R_3$ is 2- or 3-pyrryl, or preferably 2- or 3-thienyl or 2- or 3-furyl, each of which is unsubstituted or is substituted, especially in the 4-position, by $C_1$-$C_4$alkyl, such as methyl, trifluoromethyl or by $C_1$-$C_4$alkoxycarbonyl, such as methoxycarbonyl, $R_4$ is carboxy, and $R_5$ is hydrogen, and the chain carbon atom bonded to the sulfur atom preferably has the (S)-configuration and the chain carbon atom carrying the hydroxy group preferably has the (R)-configuration and the double bond joined to the radical alk is preferably in the cis-configuration and the other additional double bond is preferably in the trans-configuration, and to their salts, especially pharmaceutically acceptable salts.

The invention relates most especially to compounds of formula Ia in which $R_1$ is $C_1$-$C_4$alkyl, such as methyl, $R_2$ is $C_1$-$C_4$alkyl, such as propyl, X is oxy, alk is $C_2$-$C_5$alkylene, such as ethylene, 1,3-propylene or 1,4-butylene, n is 2, $R_3$ is 3-thienyl or 3-furyl each of which is unsubstituted or is mono- or di-substituted, especially in the 2- and/or 5- position, by halogen having an atomic number of up to and including 35, such as chlorine, $R_4$ is carboxy, and $R_5$ is hydrogen, and the chain carbon atom bonded to the sulfur atom preferably has the (S) configuration and the chain carbon atom carrying the hydroxy group preferably has the (R) configuration and the double bond joined to the radical alk is preferably in the cis-configuration and the other additional double bond is preferably in the trans-configuration, and to their salts, especially pharmaceutically acceptable salts.

The invention relates specifically to the compounds of formula I mentioned in the Examples and to their salts, especially pharmaceutically acceptable salts.

The process according to the invention for the preparation of compounds of formula I and their salts is based on methods known per se and is carried out as follows: an epoxide of formula II

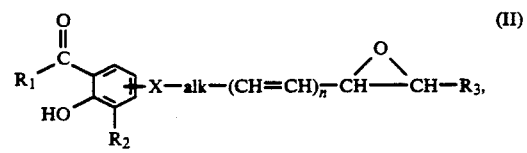

in which $R_1$, $R_2$, X, alk, n and $R_3$ are as defined above, is reacted with a thiol of formula III

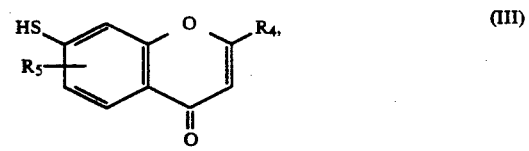

in which $R_4$ and $R_5$ are as defined above, or with a salt thereof, and, if desired, a compound obtainable in accordance with the process is converted into a different compound of formula I, a stereoisomeric mixture obtainable in accordance with the process is separated into its components and/or a free compound obtainable in accordance with the process is converted into a salt, or a salt obtainable in accordance with the process is converted into the free compound or into a different salt.

In the reaction of epoxides II with thiols III, the configuration at the carbon atom bonding with the thio group is reversed and the configuration at the carbon atom carrying the hydroxy group is retained. In order to obtain the preferred compounds having the opposite configuration at these two carbon atoms, it is therefore preferable to use the corresponding trans-epoxides II as starting materials. Starting from R,R-epoxides II there are obtained compounds I having the S(C—S—) and R(C—OH)-configurations, and starting from S,S-epoxides II there are obtained compounds I having the R(C—S—) and S(C—OH)-configurations. The reaction is effected under conditions known per se at a temperature of from approximately −20° C. to approximately +50° C., preferably at room temperature, that is to say from 18° C. to 25° C., and especially in a basic medium, for example in the presence of an amine, especially a tertiary aliphatic, arylaliphatic or saturated heterocyclic amine, such as a trialkylamine (for example triethylamine or ethyldiisopropylamine), a dialkylbenzylamine (for example N,N-dimethylbenzylamine), an N,N-dialkylaniline (for example N,N-dimethylaniline) or N-methyl- or N-ethyl-piperidine or N,N'-dimethylpiperazine. The reaction is usually carried out in an inert organic solvent, such as a lower alkanol, for example methanol or ethanol.

In a preferred embodiment, components II and III in which $R_4$ is esterified carboxy or tetrazolyl and $R_3$ is as defined above and is, for example, esterified carboxy or unsubstituted or fluorinated lower alkyl, are used as starting materials and $R_4$ is hydrolysed (optionally selectively) to carboxy, which is then converted, if desired, into amidated carboxy. Starting materials for the process according to the invention are either known per se or can be obtained in a manner known per se by known analogy processes.

The epoxide of the above-defined formula II used as starting material can be prepared especially by means of the same processes as those used in the synthesis of leucotrienes. In a typical general method of synthesis for compounds II in which n is 1, for example an aldehyde of formula

  (IV), in which A and $R_3$ are as defined above, is used as starting material, a free carboxy group $R_3$ which may be present being protected in the form of an ester, for example a lower alkyl ester. This compound is condensed with formylmethylenetriphenylphosphorane (or an equivalent reagent), the corresponding trans-3-$R_3$-prop-2-enal of formula

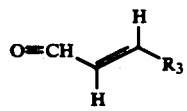  (V)

being formed. This compound is then epoxidised in a manner known per se, preferably under weakly alkaline conditions (for example in the presence of alkali carbonates), with aqueous hydrogen peroxide, to produce a trans-, that is to say 2(RS),3(RS)-epoxy-3-$R_3$-propanal of formula

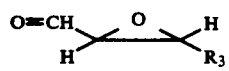  (VI)

The epoxyaldehyde VI can then be reacted to form the corresponding epoxide II in which $R_4$ is esterified carboxy and n is 1 by condensation with a phosphonium halide

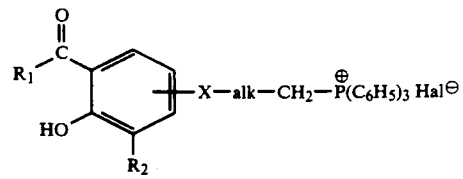  (VII)

in which $R_1$, $R_2$ and alk are as defined above and Hal is a halogen atom, preferably bromine, and with a base, for example sodium amide, in tetrahydrofuran.

Compounds VII are prepared especially by reaction of a corresponding compound of formula

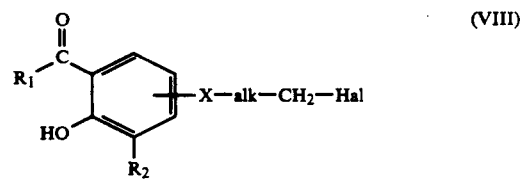  (VIII)

with triphenylphosphine in customary manner. Compounds VIII in which X is oxy or thio are obtained, for example, by condensing with one another corresponding compounds of formulae

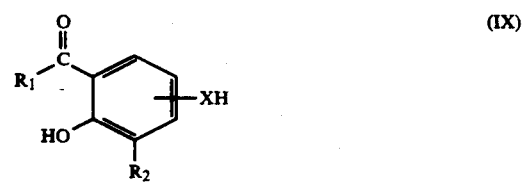  (IX)

and

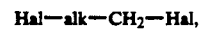  (X)

in customary manner.

In another method of preparing compounds II, trans-3-$R_3$-prop-2-enol of formula

  (XI)

in which $R_3$ is as defined above, but free carboxy as a substituent of $R_3$ is preferably protected in an ester form, is converted, for example, by treatment with an N-haloamide, such as a lower alkanecarboxylic acid (N-halogen)amide, for example N-bromoacetamide, or with an aliphatic or aromatic dicarboxylic acid amide, such as N-bromosuccinimide or N-chlorophthalimide, into the corresponding halohydrin of formula

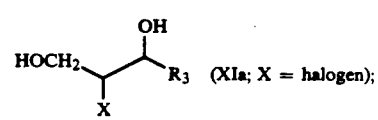  (XIa; X = halogen);

this is dehydrohalogenated by treatment with a base, for example treatment with sodium hydroxide in ethanol/water, and the resulting methylol epoxide of formula

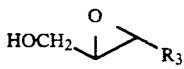

is oxidised in customary manner, for example with chromium trioxide in dichloromethane, to the epoxyaldehyde of formula

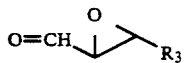

Especially advantageous is another method for the preparation of intermediates formula II that leads with fewer steps to sterically uniform products but is generally not easy to carry out. It is based on the principle of epoxidising the trans-propenol XI, for example by means of tert.-butyl hydroperoxide in the presence of titanium tetraisopropanolate and a D- or L-tartaric acid di-lower alkyl ester, and when a D-tartaric acid ester is used predominantly 2R,3R-epoxy-3-$R_3$-propanol XIIa is obtained, and when an L-tartaric acid ester is used predominantly the corresponding 2S,3S-epoxy-3-$R_3$-propanol XIIb is obtained

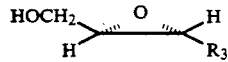

and

This compound is then oxidised, for example by treatment with oxalyl chloride/dimethyl sulfoxide and then with triethylamine, to the corresponding epoxyaldehyde VI which can then be reacted with the corresponding phosphonium salt VII to form the corresponding epoxide II in which $R_3$ is esterified carboxy and n is 1.

In that reaction there are obtained predominantly epoxides II in which the double bond has the preferred cis-stereoconfiguration. If a D-tartaric acid ester is used, then, as mentioned above, there are obtained predominantly compounds II in which the epoxy group has the R,R-configuration, or S,S-enantiomers if the reaction is carried out in the presence of L-tartaric acid esters.

For the preparation of epoxides II in which n is 2, for example the epoxy alcohol XIIa or XIIb is first converted by treatment with N,N'-dicyclohexylcarbodiimide and dimethyl sulfoxide in the presence of trifluoroacetic acid and pyridine and then with triphenylphosphoranylideneacetaldehyde into the corresponding 4R,5R- or 4S,5S-4,5-epoxy-5-$R_3$-pent-2-enal of formula XIIIa or XIIIb, respectively

or

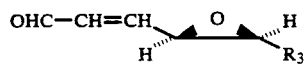

which is then reacted further with the phosphonium halide VII to form the corresponding epoxide II in which n is 2. It is preferable to obtain those epoxides in which the double bond joined to the radical alk has cis-stereoconfiguration and the double bond joined to the oxirane ring has trans-stereoconfiguration.

Compounds obtainable in accordance with the process can, if desired, be converted into other compounds of formula I.

For example, esterified or amidated carboxy groups can be hydrolysed to free hydroxy, preferably under basic conditions, for example in the presence of sodium hydroxide solution, and preferably in a water-miscible organic solvent, such as tetrahydrofuran, dioxane or a lower alkanol, such as methanol or ethanol. Starting from compounds I in which $R_4$ is esterified carboxy, such as lower alkoxycarbonyl, and $R_3$ contains such a group as substituent, the hydrolysis can be controlled in such a manner that selectively only $R_4$ or both $R_4$ and the lower alkoxycarbonyl substituent of $R_3$ are hydrolysed to carboxy. If an equimolar sodium hydroxide solution is used and mild reaction conditions are chosen, for example stirring at room temperature for about 0.5 to 2 hours, virtually only alkoxycarbonyl $R_4$ is hydrolysed, whilst under extreme conditions, for example with prolonged reaction periods or with heating, both $R_4$ and the alkoxycarbonyl group in $R_3$ are hydrolysed to carboxy.

Conversely, carboxy $R_4$ and a carboxy substituent of $R_3$ can be esterified in customary manner.

Furthermore, free or esterified carboxy $R_4$ and such a group as a substituent of $R_3$ can be amidated in customary manner, for example by treatment with ammonia or with a mono-or di-lower alkylamine. For example, carboxy $R_4$ can be converted in customary manner, for example in the presence of a carbodiimide salt, for example N-ethyl-N'-(3-dimethylaminopropyl)-carbodiimide hydrochloride, and 4-dimethylaminopyridine, with an unsubstituted or substituted benzenesulfonamide into the corresponding N-benzenesulfamidoylcarbamoyl groups.

Of course, it is also possible to separate resulting diastereoisomeric mixtures into the individual components on the basis of the different physical properties of the components and/or to separate resulting mixtures of enantiomers into the individual enantiomers according to customary racemate separation processes. If individual diastereoisomers are desired, then advantageously an individual diastereoisomer of a starting material can be used at any stage or one diastereoisomer can be preferentially formed from a starting material in diastereoisomer form by means of stereoselective reaction conditions or optically active reagents, or racemic diastereoisomeric mixtures can be separated into the individual diastereoisomers by physical separation methods, optionally using optically active auxiliaries.

From the stereochemical standpoint, however, both the condensation according to the invention of components II and III and the preparation of the starting materials are preferably carried out using starting materials that are uniform in stereoconfiguration in each case, where possible carrying out the reactions stereoselectively, for example by the use of configuratively uniform, optically active reagents and/or auxiliaries, and isolating configuratively uniform products from reaction mixtures immediately after the reaction. For example, in the preparation of the unsaturated starting material, cis- and transisomers which may be formed are separated from one another immediately, for which purpose the customary physical separation methods, such as, especially, chromatography, are suitable. In the main reaction there is used especially the stereoisomeric epoxide II having the stereoconfiguration of the double bond(s) that is preferred in the end product, which is in racemic form (which is often formed in the variant of the epoxidisation of the compound V with hydrogen peroxide) or which is preferably in the form of an individual diastereoisomer in which the configuration at the oxirane carbon atom making a bond with the S atom is opposite to the configuration at the (C—S—) carbon atom preferred in the end product I.

Likewise, resulting salts can be converted, for example by treatment with an acid, into the free acids, and resulting free acids can be converted by treatment with a base into salts.

As a result of the close relationship between the novel compounds in free form and in the form of their salts, hereinbefore and hereinafter the free compounds and their salts should be understood, where appropriate, as meaning also the corresponding salts and free compounds, respectively.

The invention relates also to those forms of the process according to which a compound obtainable as intermediate at any stage of the process is used as starting material and the remaining steps are carried out or a starting material is used in the form of a salt or is formed under the reaction conditions.

The invention relates also to the novel starting materials and intermediates occurring in the processes according to the invention and their preliminary stages.

Preferably, the starting materials used and the reaction conditions chosen are such that the compounds listed above as being especially preferred are obtained.

The present invention relates also to pharmaceutical preparations and medicaments that contain one of the compounds of formula I according to the invention or a pharmaceutically acceptable salt thereof. The pharmaceutical preparations according to the invention are especially those which are intended for local administration and especially for administration by inhalation, for example in the form of an aerosol, a micronised powder or a fine spray solution, to mammals, especially humans, and which contain the active ingredient on its own or together with a pharmaceutically acceptable carrier.

Pharmaceutical preparations for topical and local use are, for example for the treatment of the skin, lotions and creams that contain a liquid or semi-solid oil-in-water or water-in-oil emulsion, and ointments (which preferably contain a preservative). Suitable for the treatment of the eyes are eye drops that contain the active ingredient in aqueous or oily solution, and eye ointments, which are preferably manufactured in sterile form. Suitable for the treatment of the nose are aerosols and sprays (similar to those described below for the treatment of the respiratory tract), coarse powders, which are administered by rapid inhalation through the nostrils, and especially nose drops, which contain the active ingredient in aqueous or oily solution; suitable for local treatment of the buccal cavity are lozenges that contain the active ingredient in a mass generally formed from sugar and gum arabic or tragacanth, to which flavourings may be added, and pastilles that contain the active ingredient in an inert mass, for example of gelatine and glycerol or sugar and gum arabic.

Pharmaceutical preparations suitable for administration in the form of aerosols or sprays are, for example, solutions, suspensions or emulsions of the compound of formula I according to the invention with a suitable pharmaceutically acceptable solvent, such as, especially, ethanol and water, or a mixture of such solvents. They may, as necessary, contain other pharmaceutical adjuncts, such as non-ionic or anionic surface-active agents, emulsifiers and stabilisers, and also active ingredients of other kinds, and especially advantageously they can be mixed with a propellant gas, such as an inert gas under elevated pressure or especially with a readily volatile liquid, preferably a liquid that boils under normal atmospheric pressure below customary room temperature (for example from approximately $-30°$ to $+10°$ C.), such as an at least partially fluorinated polyhalogenated lower alkane, or a mixture of such liquids. Such pharmaceutical preparations, which are used predominantly as intermediates or stock mixtures for the preparation of the corresponding medicaments in finished form, contain the active ingredient customarily in a concentration of from approximately 0.1 to approximately 10% by weight, especially from approximately 0.3 to approximately 3% by weight. For the preparation of medicaments in finished form, such a pharmaceutical preparation is introduced into suitable containers, such as flacons and pressurised bottles, which are provided with a spray device or valve suitable for such purposes. The valve is preferably constructed in the form of a metering valve which on operation releases a predetermined amount of liquid, corresponding to a predetermined dose of the active ingredient. In the preparation of the finished medicament form, it is also possible for corresponding amounts of the pharmaceutical preparation in stock solution form and of the propellant to be introduced separately into the containers and to be mixed with one another only at that stage. The dosage of the compound of formula I to be administered and the frequency of administration depend upon the effectiveness and the duration of action of each individual compound, upon the severity of the disease to be treated and its symptoms, and upon the sex, age, weight and individual responsiveness of the mammal to be treated. On average, the recommended daily dose of a compound of formula I according to the invention for a mammal (especially a human) weighing 75 kg might be in the region of from approximately 10 to approximately 500 mg, preferably from approximately 25 to approximately 250 mg, which can advantageously be administered in several doses per day, as necessary.

The invention relates also to the use of the active ingredients of formula I according to the invention for alleviating or eliminating pathological conditions and/or symptoms of the body of a mammal, especially of a human, that can be attributed to the action of leucotrienes and occur especially in asthma. This use or the corresponding curative method, comprises the treatment of the affected body or part of the body with an anti-allergically effective amount of a compound of formula I on its own or in the form of a medicament, especially a pharmaceutical preparation intended for inhalation. The expression "an anti-allergically effective amount" is to be understood as being that amount of the active ingredient which is sufficient to produce a significant inhibition of the contractions caused by leucotrienes.

The following Examples illustrate the present invention in more detail but do not limit the scope thereof. All temperatures are given in degrees Celsius.

EXAMPLE 1

7-[(1RS,2SR)-1-Hydroxy-(5-chlorothiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid methyl ester A solution of 0.8 g of (1RS,2SR)-1,2-epoxy-1-(5-chlorothiophen-2-yl)-10-(4-acetyl-3-hydroxy-2-propylphenoxy)-deca-3(E),5(Z)-diene in 25 ml of methanol is stirred for 20 hours at room temperature under argon with 0.75 g of triethylamine and 0.6 g of 7-mercaptochromone-2-carboxylic acid methyl ester and then concentrated by evaporation. The residue is dissolved in ethyl acetate and filtered over silica gel. The filtrate is washed with 2N hydrochloric acid and saturated sodium chloride solution, dried over sodium sulfate and concentrated by evaporation. Purification of the residue by chromatography on silica gel with ethyl acetate/hexane (1:1) yields the tile compound.

The starting material can be prepared, for example, as follows:

a) 5-Chlorothiophene-2-aldehyde is prepared from 2-chlorothiophene analogously to the method described by W. J. King and F. F. Nord, J. Org. Chem. 13, 635 (1948)

b) 3-(5-Chlorothiophen-2-yl)-propenoic acid is prepared from 5-chlorothiophene-2-aldehyde according to a) analogously to the method described by W. J. King and F. F. Nord, J. Org. Chem. 14, 405 (1949)

c) 3-(5-Chlorothiophen-2-yl)-prop-2-enol 0.05 ml of dimethylformamide is added to a stirred suspension of 1.9 g of 3-(5-chlorothiophen-2-yl)-propenoic acid according to b) and 1.3 ml of oxalyl chloride in 40 ml of ether/tetrahydrofuran (1:1). The mixture is stirred at room temperature for 2 hours, then the clear solution is decanted off from the insoluble material and the solvent is removed in vacuo. The crude acid chloride is obtained in the form of a pale yellow solid. A solution of this acid chloride in 40 ml of ether/tetrahydrofuran (1:1) is added dropwise to a suspension of 250 mg of lithium aluminium hydride in 30 ml of ether/tetrahydrofuran (1:1) and the mixture is stirred at room temperature for 2 hours. The reaction mixture is then poured onto 100 ml of water and 30 ml of 1N sodium hydroxide solution and extracted with ether (3×30 ml). The combined extracts are dried over sodium sulfate, concentrated by evaporation and chromatographed on silica gel with dichloromethane/acetone (89:1). The title compound is obtained in the form of a yellow oil.

d) (2RS,3SR)-2,3-Epoxy-3-(5-chlorothiophen-2-yl)-propanol 0.75 g of m-chloroperbenzoic acid is added to a stirred solution of 0.6 g of 3-(5-chlorothiophen-2-yl)-prop-2-enol according to c) in 50 ml of dichloromethane. The solution is stirred at room temperature for 5 hours, washed with 10% sodium carbonate solution, dried over sodium sulfate and concentrated by evaporation. The residue is chromatographed on silica gel with ether and the title compound is obtained in the form of a light-yellow oil.

e) (2RS,3SR)-2,3-Epoxy-3-(5-chlorothiophen-2-yl)-propanal

A solution of 0.6 ml of dimethyl sulfoxide in 2 ml of dichloromethane is added with stirring, at −60° C., to a solution of 0.37 ml of oxalyl chloride in 10 ml of dichloromethane in a nitrogen atmosphere. After the mixture has been stirred for 5 minutes at −60° C. there is added thereto, over a period of 20 minutes, a solution of 0.7 g of (2RS,3SR)-2,3-epoxy-3-(5-chlorothiophen-2-yl)-propanol according to d) in 10 ml of dichloromethane. After a further 20 minutes at −60° C. 1.3 ml of triethylamine is added, the mixture is allowed to come to room temperature, washed with water, and dried over sodium sulfate. Filtration and concentration by evaporation yields the crude title compound in the form of a dark viscous oil.

f) (4RS,5SR)-4,5-Epoxy-5-(5-chlorothiophen-2-yl)-pent-2-enal

A mixture of 0.4 g of crude (2RS,3SR)-2,3-epoxy-3-(5-chlorothiophen-2-yl)-propanal according to e) and 0.5 g of formyltriphenylphosphorane in 15 ml of benzene is stirred at room temperature for 4 hours. The clear solution is decanted off from the undissolved material and concentrated by evaporation. The residue is taken up in ether, decanted off from the undissolved material and again concentrated by evaporation. Chromatography with ether/hexane (2:1) on silica gel yields the title compound in the form of a pale-yellow solid.

g) (1RS,2SR)-1,2-Epoxy-1-(5-chlorothiophen-2-yl)-10-(4-acetyl-3-hydroxy-2-propylphenoxy)-deca-3(E),5(Z)-diene A suspension of 5.6 g of 3-(4-acetyl-3-hydroxy-2-propylphenoxy)pentyltriphenylphosphon ium bromide in 80 ml of tetrahydrofuran is stirred for 1 hour at room temperature under argon with 0.75 g of sodium hydride and 55 mg of potassium tert.-butoxide, cooled to 0°–5° C., over a period of 5 minutes 1.6 g of (4RS,5SR)-4,5-epoxy-5-(5-chlorothiophen-2-yl)-pent-2-enal according to f) in 20 ml of tetrahydrofuran are added thereto, and then the mixture is stirred at room temperature for 2 hours. The suspension formed is poured onto phosphate buffer (pH 7) and extracted with ether. The combined ether extracts are washed with phosphate buffer (pH 7), dried over sodium sulfate and concentrated by evaporation. The residue is taken up in hexane/ethyl acetate/triethylamine (24:71:5) and filtered over silica gel prewashed with that solvent mixture. The filtrate is concentrated by evaporation and yields the title compound in the form of a light-yellow oil.

EXAMPLE 2

7-[(1RS,2SR)-1-Hydroxy-(5-chlorothiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid sodium salt 0.4 g of the methyl ester of the title compound are dissolved in 10 ml of tetrahydrofuran under argon, 3 ml of 0.2N sodium hydroxide solution are added and the mixture is stirred at room temperature for 3 hours. Concentration by evaporation and chromatographic purification of the residue on a reversed phase silica gel column (e.g. Merck Lichroprep ® RP-8) with methanol/water (3:1) yields the title compound.

EXAMPLE 3

The following may be prepared analogously to Examples 1 and 2:

7-[(1RS,2SR)-1-hydroxy-(4-chlorothiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid, its methyl ester and its sodium salt, starting from 4-chlorothiophene-2-aldehyde;

7-[(1RS,2SR)-1-hydroxy-(thiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid, its methyl ester and its sodium salt, starting from thiophene-2-aldehyde;

7-[(1RS,2SR)-1-hydroxy-(thiophen-3-yl)-10-(4-acetyl-3-hydroxy-2-propylphenoxy)-deca-3(E),5(Z)-dien-2-ylthio]-4-oxo-4H-1-benzopyrane-2-carboxylic acid, its methyl ester and its sodium salt, starting from thiophene-3-aldehyde;

7-[(1RS,2SR)-1-hydroxy-(5-fluorothiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid, its methyl ester and its sodium salt, starting from 5-fluorothiophene-2-aldehyde; 7-[(1RS,2SR)-1-hydroxy-(5-trifluoromethylthiophen-2-yl)-10-(4-acetyl-3-hydroxy-2-propylphenoxy)-deca-3(E),5(Z)-dien-2-ylthio]-4-oxo-4H-1-benzo pyrane-2-carboxylic acid, its methyl ester and its sodium salt, starting from 2-trifluoromethylthiophene and 7-[(1RS,2SR)-1-hydroxy-(4-trifluoromethylthiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid, its methyl ester and its sodium salt, starting from 3-trifluoromethylthiophene.

EXAMPLE 4

7-[(1R,2S)-1-Hydroxy-1-(5-trifluoromethylfur-2-yl)-10-(4-acetyl-3-hydroxy-2-propylphenoxy)-deca-3(E),5(Z)-dien-2-ylthio]-4-oxo-4H-1-benzopyrane-2-carboxylic acid methyl ester 4.02 g of 7-mercapto-4-oxo-4H-1-benzopyrane-2-carboxylic acid methyl ester are added to a solution of 7.16 g of (1R,2R)-1,2-epoxy-1-(5-trifluoromethylfur-2-yl)-10-(4-acetyl-3-hydroxy-2-propylphenoxy)-deca-3(E),5(Z)-diene in 100 ml of methanol and 7.2 ml of triethylamine and the mixture is stirred at room temperature for 16 hours. The light-brown suspension is concentrated by evaporation, dissolved in 170 ml of ethyl acetate and filtered over a silica gel cake. The filtrate is washed with N-hydrochloric acid, saturated sodium chloride solution, water and brine, dried over magnesium sulfate and concentrated by evaporation. Purification of the residue on a column (Merck, LiChroprep ® Si 60) with hexane:ethyl acetate (1:1) yields the title compound in the form of a light-yellow solid foam.

The starting materials are prepared as follows:

a) 3-(5-Trifluoromethylfur-2-yl)-2(E)-propenoic acid methyl ester 20.8 ml of phosphonoacetic acid triethyl ester in 20 ml of tetrahydrofuran are added at 20°-30° over a period of 30 minutes to a suspension of 3.15 g of sodium hydride (80% suspension in white oil) in 80 ml of tetrahydrofuran (exothermic, cooling). After a further 30 minutes at 20°-30°, 16.4 g of 5-trifluoromethylfurane-2-carboxaldehyde in 25 ml of tetrahydrofuran are added dropwise over a period of 30 minutes and the mixture is stirred for 90 minutes at room temperature. 100 ml of water are added dropwise to the reaction mixture, and the mixture is extracted with ethyl acetate. The combined organic phases are dried over magnesium sulfate and concentrated by evaporation. The title compound is thus obtained in the form of a colourless oil.

b) 3-(5-Trifluoromethylfur-2-yl)-2(E)-propenol 225 ml of a 1 molar diisobutylaluminium hydride solution in hexane are added at 0°-10° over a period of 30 minutes to a solution of 23.4 g of 3-(5-trifluoromethylfur-2-yl)-2(E)-propenoic acid methyl ester in 100 ml of diethyl ether. After a further 30 minutes' stirring at 0°-10° the reaction mixture is poured onto a mixture of 280 g of ice and 45 ml of concentrated hydrochloric acid and stirred until two clear phases have formed. The organic phase is dried over magnesium sulfate and concentrated by evaporation to yield the title compound in the form of a colourless oil.

c) (2R,3R)-2,3-Epoxy-3-(5-trifluoromethylfur-2-yl)-propanol 8 g of pulverised molecular sieve 4 Å are added to a solution of 18.1 g of tetraisopropyl orthotitanate in 400 ml of methylene chloride, the mixture is cooled to from −70° to −75° and, with stirring, 15.6 g of D(−)-tartaric acid diethyl ester and 25.2 g of 3-(5-trifluoromethylfur-2-yl)-2(E)-propenol are added. After the mixture has been stirred for 15 minutes at from −70° to −75°, 117 ml of tert.-butylhydroperoxide (3-molar in toluene) are added dropwise thereto over a period of 20 minutes. After a further hour at from −65° to −70°, the temperature is allowed to rise to 0° over a period of 2 hours. The resulting light-yellow solution is poured into a solution of 71 g of iron(II) sulfate-heptahydrate and 28.2 g of L(+)-tartaric acid in 300 ml of water. The mixture is then stirred for 30 minutes at 0°-10° and extracted with diethyl ether. The organic phases are dried over sodium sulfate and concentrated by evporation. The residue is dissolved in 450 ml of diethyl ether, at 0°-5° a suspension of 11.3 g of sodium hydroxide in 300 ml of saturated sodium chloride solution is added, and the reaction mixture is stirred for 1 hour at 0°-5°. The organic phase is separated off and the aqueous phase is extracted with diethyl ether. The combined organic phases are dried and concentrated by evporation. The residue is purified on a silica gel column (Merck LiChroprep ® Si 60) with hexane/ethyl acetate (1:1). The title compound is thus obtained in the form of a colourless oil.

d) (4R,5R)-4,5-Epoxy-5-(5-Trifluoromethylfur-2-yl)-pent-2(E)-enal 110 g of sulfur trioxide/pyridine complex dissolved in 350 ml of dimethyl sulfoxide are added at 20°-22°, over a period of 30 minutes, to a solution of 65.3 g of (2R,3R)-2,3-epoxy-3-(5-trifluoromethylfur-2-yl)-propanol in 700 ml of dimethyl sulfoxide and 96 ml of triethylamine (exothermic, cooling). After the mixture has been stirred for a further 30 minutes, 86 g of formylmethylenetriphenylphosphorane are added in portions over a period of 1 hour, and the reaction mixture is stirred for 18 hours at room temperature. After the addition of 2 liters of ethyl acetate, the reaction mixture is washed with phosphate buffer (pH 7). The organic phase is dried over sodium sulfate and concentrated by evaporation. The residue is suspended in 400 ml of hexane/ethyl acetate (4:1) and the suspension is stirred for 15 minutes then filtered with suction. The residue is washed with hexane/ethyl acetate (4:1) and the filtrate is concentrated by evaporation. The residue is purified on a column (Merck LiChroprep ® silica gel 60) with hexane/ethyl acetate (3:1). The title compound is thus obtained in the form of a light-yellow oil.

e) (1R,2R)-1,2-Epoxy-1-(5-trifluoromethylfur-2-yl)-10-(4-acetyl-3-hydroxy-2-propylphenoxy)-deca-3(E),5(Z)-diene 8.63 g of (4R,5R)-4,5-epoxy-5-(5-trifluoromethylfur-2-yl)-pent-2(E)-enal in 20 ml of tetrahydrofuran and then 4.16 g of sodium amide powder are added in small portions to a suspension of 31.9 g of 3-(4-acetyl-3-hydroxy-2-propylphenoxy)-pentyltriphenylphosphonium bromide in 120 ml of tetrahydrofuran. The reaction mixture is stirred for 2 hours at 20°-25° and filtered with suction. The residue is washed with tetrahydrofuran. Phosphate buffer (pH 7) is added to the filtrate and extraction is carried out with diethyl ether. The combined organic phases are dried over sodium sulfate and concentrated by evaporation. The residue is taken up in 250 ml of hexane/ethyl acetate + 1% triethylamine and filtered over a silica gel cake that has been pre-washed with the same solvent mixture. The filtrate is concentrated by evaporation and the residue is purified on a column (Merck LiChroprep® Si 60) with hexane/ethyl acetate (7:3 + 1% triethylamine). The title compound is obtained in the form of a light-yellow oil.

EXAMPLE 5

7-[(1R,2S)-1-Hydroxy-1-(5-trifluoromethylfur-2-yl)-10-(4-acetyl-3-hydroxy-2-propylphenoxy)-deca-3(E),5(Z)-dien-2-ylthio]-4-oxo-4H-1-benzopyrane-2-carboxylic acid sodium salt Under argon, 0.71 g of the methyl ester of Example 4 is dissolved in 20 ml of tetrahydrofuran, 5 ml of 0.2N NaOH are added and the mixture is stirred at room temperature for 1 hour. Concentration by evaporation and purification of the residue on a column (MERCK LiChroprep RP-8) with MeOH:H₂O=3:1 yields the title compound. M.p. 204°-207°.

EXAMPLE 6

The following can be prepared analogously to Examples 1-5:

7-[(1R,2S)-1-hydroxy-1-(5-trifluoromethylfur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-methylfur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(5-methylfur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-chlorofur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(5-chlorofur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-fluorofur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(5-fluorofur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-methoxycarbonylfur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(5-methoxycarbonylfur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-carboxyfur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its disodium salt;

7-[(1R,2S)-1-hydroxy-1-(5-carboxyfur-2-yl)-8-(4-acetyl-3-hydroxy-2-propylphenoxy)octa-3(E),5(Z)-dien-2-ylthio]-4-oxo-4H-1-benzopyrane-2-carboxylic acid and its disodium salt;

7-[(1R,2S)-1-hydroxy-1-(4-trifluoromethylfur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(4-trifluoromethylfur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(4-methylfur-2-yl)-10-(4-acetyl-3-hydroxy-2-propylphenoxy)deca-3(E),5(Z)-dien-2-ylthio]-4-oxo-4H-1-benzopyrane-2-carboxylicacid and its sodium salt;

7-[(1R,2S)-1-hydroxy-1-(4-methylfur-2-yl)-8-(4-acetyl-3-hydroxy-2-propylphenoxy)octa-3(E),5(Z)-dien-2-ylthio]-4-oxo-4H-1-benzopyrane-2-carboxylic acid and its sodium salt;

7-[(1R,2S)-1-hydroxy-1-(4-chlorofur-2-yl)-10-(4-acetyl-3-hydroxy-2-propylphenoxy)deca-3(E),5(Z)-dien-2-ylthio]-4-oxo-4H-1-benzopyrane-2-carboxylic acid and its sodium salt;

7-[(1R,2S)-1-hydroxy-1-(4-chlorofur-2-yl)-8-(4-acetyl-3-hydroxy-2-propylphenoxy)octa-3(E),5(Z)-dien-2-ylthio]-4-oxo-4H-1-benzopyrane-2-carboxylic acid and its sodium salt;

7-[(1R,2S)-1-hydroxy-1-(4-fluorofur-2-yl)-10-(4-acetyl-3-hydroxy-2-propylphenoxy)deca-3(E),5(Z)-dien-2-ylthio]-4-oxo-4H-1-benzopyrane-2-carboxylic acid and its sodium salt;

7-[(1R,2S)-1-hydroxy-1-(4-fluorofur-2-yl)-8-(4-acetyl-3-hydroxy-2-propylphenoxy)octa-3(E),5(Z)-dien-2-ylthio]-4-oxo-4H-1-benzopyrane-2-carboxylic acid and its sodium salt;

7-[(1R,2S)-1-hydroxy-1-(4-methoxycarbonylfur-2-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(4-methoxycarbonylfur-2-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

-(1R,2S)-1-hydroxy-1-(4-carboxyfur-2-yl)-10-(4-acetyl-3-hydroxy-2-propylphenoxy)deca-3(E),5(Z)-dien-2-ylthio]-4-oxo-4H-1-benzopyrane-2-carboxylic acid and its disodium salt;

7-[(1R,2S)-1-hydroxy-1-(4-carboxyfur-2-yl)-8-(4-acetyl-3-hydroxy-2-propylphenoxy)octa-3(E),5(Z)-dien-2-ylthio]-4-oxo-4H-1-benzopyrane-2-carboxylic acid and its disodium salt;

7-[(1R,2S)-1-hydroxy-1-(5-trifluoromethylfur-3-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(5-trifluoromethylfur-3-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-methylfur-3-yl)-10-(4-acetyl-3-hydroxy-2-propylphenoxy)deca-3(E),5(Z)-dien-2-ylthio]-4-oxo-4H-1-benzopyrane-2-carboxylic acid and its sodium salt;

7-[(1R,2S)-1-hydroxy-1-(5-methylfur-3-yl)-8-(4-acetyl-3-hydroxy-2-propylphenoxy)octa-3(E),5(Z)-dien-2- ylthio]-4-oxo-4H-1-benzopyrane-2-carboxylic acid and its sodium salt;

7-[(1R,2S)-1-hydroxy-1-(5-chlorofur-3-yl)-10-(4-acetyl-3-hydroxy-2-propylphenoxy)deca-3(E),5(Z)-dien-2-ylthio]-4-oxo-4H-1-benzopyrane-2-carboxylic acid and its sodium salt;

7-[(1R,2S)-1-hydroxy-1-(5-chlorofur-3-yl)-8-(4-acetyl-3-hydroxy-2-propylph enoxy)octa-3(E),5(Z)-dien-2-ylthio]-4-oxo-4H-1-benzopyrane-2-carboxylic acid and its sodium salt;

7-[(1R,2S)-1-hydroxy-1-(5-fluorofur-3-yl)-10-(4-acetyl-3-hydroxy-2-propylphenoxy)deca-3(E),5(Z)-dien-2-ylthio]-4-oxo-4H-1-benzopyrane-2-carboxylic acid and its sodium salt;

7-[(1R,2S)-1-hydroxy-1-(5-fluorofur-3-yl)-8-(4-acetyl-3-hydroxy-2-propylphenoxy)octa-3(E),5(Z)-dien-2-ylthio]-4-oxo-4H-1-benzopyrane-2-carboxylic acid and its sodium salt;

7-[(1R,2S)-1-hydroxy-1-(5-methoxycarbonylfur-3-yl)-10-(4-acetyl 3-hydroxy-2-propylphenoxy)-deca-3(E),5(Z)-dien-2-ylthio]-4-oxo-4H-1-benzopyrane-2-carboxylic acid and its sodium salt;

7-[(1R,2S)-1-hydroxy-1-(5-methoxycarbonylfur-3-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1R,2S)-1-hydroxy-1-(5-carboxyfur-3-yl)-10-(4-acetyl-3-hydroxy-2-propylphenoxy)deca-3(E),5(Z)-dien-2-ylthio]-4-oxo-4H-1-benzopyrane-2-carboxylic acid and its disodium salt and 7-[(1R,2S)-1-hydroxy-1-(5-carboxyfur-3-yl)-8-(4-acetyl-3-hydroxy-2-propylphenoxy)octa-3(E),5(Z)-dien-2-ylthio]-4-oxo-4H-1-benzopyrane-2-carboxylic acid and its disodium salt.

EXAMPLE 7

7-[(1RS,2SR)-1-hydroxy-1-(thiophen-3-yl)-8-(4-acetyl-3-hydroxy-2-propylphenoxy)-octa-3(E),5(Z)-dien-2-ylthio]-4-oxo-4H-1-benzopyrane-2-carboxylic acid methyl ester A solution of 0.4 g of (1RS,2SR)-1,2-epoxy-1-(thiophen-3-yl)-8-(4-acetyl-3-hydroxy-2-propylphenoxy)-octa-3(E),5(Z)-diene in 10 ml of methanol is stirred for 20 hours at room temperature under argon with 0.37 g of triethylamine and 0.3 g of 7-mercaptochromone-2-carboxylic acid methyl ester, and then concentrated by evaporation. The residue is dissolved in ethyl acetate and filtered over silica gel. The filtrate is washed with 2N hydrochloric acid and saturated sodium chloride solution, dried over sodium sulfate and concentrated by evaporation. Purification of the residue by chromatography on silica gel with ethyl acetate/hexane (1:1) yields the title compound.

The starting materials can be prepared, for example, as follows:

a) 3-(Thiophen-3-yl)-prop-2-enol 0.1 ml of dimethylformamide is added to a stirred suspension of 10.9 g of 3-(thiophen-3-yl)-propenoic acid and 9.3 ml of oxalyl chloride in 80 ml of ether/tetrahydrofuran (1:1). The mixture is stirred at room temperature for 2 hours and then the clear solution is decanted off from the insoluble material and the solvent is removed in vacuo. The acid chloride is obtained in the form of a pale-yellow solid. A solution of that acid chloride in 80 ml of ether/tetrahydrofuran (1:1) is added dropwise to a suspension of 1.9 g of lithium aluminium hydride in 100 ml of ether/tetrahydrofuran (1:1) and the mixture is stirred at room temperature for 2 hours. The mixture is then poured into 800 ml of water and 200 ml of 1N sodium hydroxide solution and extracted with ether (3×100 ml). The combined extracts are dried over sodium sulfate, concentrated by evaporation and chromatographed on silica gel with dichloromethane/acetone (9:1). The title compound is obtained in the form of light-yellow crystals, m.p.=58°-60° C.

b) (2RS,3SR)-2-Bromo-3-(thiophen-3-yl)-propane-1,3-diol 11.0 g of N-bromoacetamide in 100 ml of water are added to a solution, stirred at 0° C., of 9.5 g of 3-(thiophen-3-yl)-prop-2-enol in 300 ml of acetone. The reaction solution is stirred at room temperature for 14 hours, the acetone is evaporated off in vacuo and the aqueous-oily residue is extracted with 300 ml of ether. After drying over sodium sulfate and evaporating off the solvent, the residue is chromatographed on silica gel with dichloromethane/acetone (4:1). The title compound is obtained in the form of a yellow oil.

c) (2RS,3SR)-2,3-Epoxy-3-(thiophen-3-yl)-propanol 0.8 g of sodium hydroxide in 15 ml of water is added to a solution of 2.4 g of (2RS,3SR)-2-bromo-3-(thiophen-3-yl)-propane-1,3-diol in 25 ml of ethanol. The reaction mixture is stirred for 40 minutes at room temperature, the ethanol is evaporated off in vacuo and the residue is diluted with 400 ml of water. Extraction is carried out with dichloromethane (3×100 ml), the extracts are dried over sodium sulfate and the solvent is evaporated off. The residue is chromatographed on silica gel with dichloromethane/acetone (9:1). The title compound is obtained in the form of light-yellow crystals, m.p.=63°-65° C.

d) (2RS,3SR)-2,3-Epoxy-3-(thiophen-3-yl)-propanol 6.9 g of (2RS,3SR)-2,3-epoxy-3-(thiophen-3-yl)-propanol dissovled in 35 ml of dichloromethane are added to a solution of 26.5 g of chromium trioxide in 42 ml of pyridine and 660 ml of dichloromethane. The reaction mixture is stirred at room temperature for 15 minutes and decanted off from the undissolved material, and the solution is washed in succession with 100 ml each of 5% sodium hydroxide solution, 5% hydrochloric acid, 5% sodium hydrogen carbonate solution and saturated sodium chloride solution. After drying over sodium sulfate and evaporating off the solvent in vacuo, the title compound is obtained in the form of a yellow oil.

e) (4RS,5SR)-4,5-Epoxy-5-(thiophen-3-yl)-pent-2-enal 11.0 g of formyltriphenylphosphorane are added to a solution of 5.5 g of (2RS,3SR)-2,3-epoxy-3-(thiophen-3-yl)-propanol in 300 ml of dichloromethane and the reaction mixture is stirred at room temperature for 10 hours. The reaction mixture is washed with phosphate buffer pH 7 and dried over sodium sulfate and the solvent is removed in vacuo. The residue is chromatographed on silica gel with hexane/ethyl acetate (4:1). The title compound is obtained in the form of a yellow oil.

f) (1RS,2SR)-1,2-Epoxy-1-(thiophen-3-yl)-8-(4-acetyl-3-hydroxy-2-propylphenoxy)octa-3(E),5(Z)-diene A suspension of 5.0 g of 3-(4-acetyl-3-hydroxy-2-propylphenoxy)propyltriphenylphosphonium bromide in 80 ml of tetrahydrofuran is stirred for 1 hour at room temperature under argon with 0.73 g of sodium amide and 52 mg of potassium tert.-butoxide and cooled to −100° C. Over a period of 5 minutes 1.5 g of (4RS,5SR)-4,5-epoxy-5-(thiophen3-yl)-pent-2-enal in 20 ml of tetrahydrofuran are added and the reaction mixture is then stirred for 2 hours at room temperature. The resulting suspension is poured onto phosphate buffer (pH 7) and extracted with ether. The combined ether extracts are washed with phosphate buffer pH 7, dried over sodium sulfate and concentrated by evaporation. The residue is taken up in hexane/ethyl acetate/triethylamine (24:71:5) and filtered over silica gel prewashed with that solvent mixture. The filtrate is concentrated by evaporation and yields the title compound in the form of a light-yellow oil.

EXAMPLE 8

7-[(1RS,2SR)-1-Hydroxy-1-(thiophen-3-yl)-8-(4-acetyl-3-hydroxy-2-propylphenoxy)-octa-3(E),5(Z)-dien-2-yl-7-thio]-4-oxo-4H-1-benzopyrane-2-carboxylic acid sodium salt Under argon, 0.4 g of the methyl ester of the title compound according to Example 7 are dissolved in 10 ml of tetrahydrofuran, 3 ml of 0.2N sodium hydroxide solution are added and the mixture is stirred at room temperature for 3 hours. Concentration by evaporation and purification of the residue by chromatography on a reversed phase silica gel column (e.g. Merck Lichroprep ® RP-8) with methanol/water (3:1) yield the title compound in the form of a light-yellow solid having a melting point of 200°-203°.

EXAMPLE 9

7-[(1RS,2SR)-1-Hydroxy-1-(thiophen-3-yl)-8-(4-acetyl-3-hydroxy-2-propylphenoxy)-octa-3(E),5(Z)-dien-2-yl-7-thio]-4-oxo-4H-1-benzopyrane-2-carboxylic acid

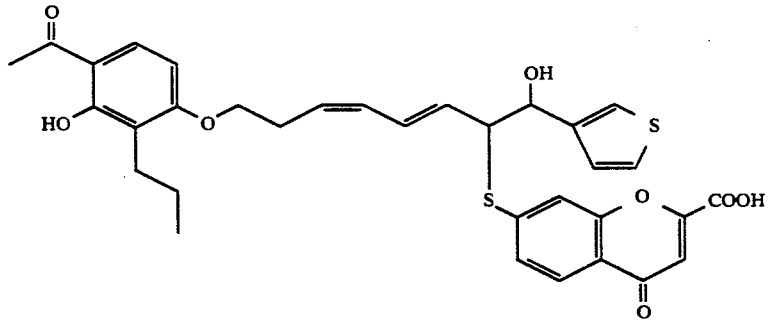

Under argon, 0.5 g of the methyl ester of the title compound (Example 7) are dissolved in 10 ml of tetrahydrofuran, 4 ml of 0.2N sodium hydroxide solution are added and the reaction mixture is stirred at room temperature for 3 hours. The reaction mixture is diluted with 50 ml of water, rendered acidic with 5 ml of 0.2N hydrochloric acid and extracted with dichloromethane. After drying over sodium sulfate and evaporating off the solvent, the residue is chromatographed on silica gel with chloroform/methanol (4:1). The title compound is obtained in the form of a light-yellow resin.

EXAMPLE 10

The following can also be prepared analogously to Examples 7 to 9:

7-(1RS,2SR)-hydroxy-1-hydroxy-1-(fur-3-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt;

7-[(1RS,2SR)-hydroxy-1-(fur-3-yl)-9-(4-acetyl-3-hydroxy-2-propylphenoxy)-nona-3(E),5(Z)-dien-2-ylthio]-4-oxo-4H-1-benzopyrane-2-carboxylic acid and its sodium salt;

7-[(1RS,2SR)-hydroxy-1-(fur-3-yl)-8-(4-acetyl-3-hydroxy-2-propylphenoxy)-octa-3(E),5(Z)-dien-2-ylthio]-4-oxo-4H-1-benzopyrane-2-carboxylic acid and its sodium salt;

7-[(1RS,2SR)-hydroxy-1-(2,5-dichlorothiophen-3-yl)-10-(4-acetyl-3-hydroxy-2-propylphenoxy)-deca-3(E),5(Z)-dien-2-ylthio]-4-oxo-4H-1-benzopyrane-2-carboxylic acid methyl ester and its sodium salt and 7-[(1RS,2SR)-hydroxy-1-(2,5-dichlorothiophen-3-yl)-10-(4-acetyl-3-hydroxy-2-propylphenoxy)-deca-3(E),5(Z)-dien-2-ylthio]-4-oxo-4H-1-benzopyrane-2-carboxylic acid and its sodium salt.

EXAMPLE 11

An inhalation suspension, containing propellant and forming a solid aerosol, containing 0.1% by weight active ingredient, e.g. 7-[(1RS,2SR)-1-hydroxy-(5-chlorothiophen-2-yl)-10-(4-acetyl-3-hydroxy-2-propylphenoxy)-deca-3(E),5(Z)-dien-2-ylthio]-4-oxo-4H-1-benzopyrane-2-carboxylic acid sodium salt, can be prepared, for example, as follows:

| Composition: | % by weight |
|---|---|
| active ingredient, micronised | 0.1 |
| sorbitan trioleate | 0.5 |
| propellant A | 4.4 |
| (trichlorotrifluoroethane) | |
| propellant B | |
| (dichlorodifluoromethane and | 15.0 |
| 1,2-dichlorotetrafluoroethane) | 80.0 |

PREPARATION

In the absence of moisture, the active ingredient is suspended in the trichlorotrifluoroethane using a customary homogeniser and with the addition of the sorbitan trioleate, and the suspension is introduced into an aerosol container provided with a metering valve; the container is sealed and filled up with propellant B under pressure.

EXAMPLE 12

An approximately 2% aqueous solution, suitable for inhalation, of an active ingredient in the form of its sodium or potassium salt, for example 7-[(1RS,2SR)-1-hydroxy-(5-chlorothiophen-2-yl)-10-(4-acetyl-3-hydroxy-2-propylphenoxy)-deca-3(E),5(Z)-dien--2-ylthio]-4-oxo-4H-1-benzopyrane-2-carboxylic acid sodium salt, can be prepared, for example, as follows:

| Composition | | |
|---|---|---|
| active ingredient (K or Na salt) | | 200 mg |
| disodium salt of ethylenediaminetetraacetic acid | | 10 mg |
| benzalkonium chloride | | 10 mg |
| water, freshly distilled | ad | 100 ml |

PREPARATION

The active ingredient is dissolved in approximately 60 ml of freshly distilled water, and the stabiliser (disodium salt of ethylenediaminetetraacetic acid) and the preservative (benzalkonium chloride) are added. When all the components have completely dissolved, the resulting solution is made up to 100 ml and introduced into small pressurised bottles which are then sealed in gas-tight manner. The propellant is added, as required, in gaseous form under pressure or in liquid form.

What is claimed is:

1. A substituted alkanophenone of the general formula in which $R_1$ is unsubstituted or fluorinated lower alkyl; $R_2$ is hydrogen, unsubstituted or fluorinated lower alkyl, or lower alkenyl; n is 1 or 2; X is lower alkylene, oxy, thio or a direct bond; alk is lower alkylene; $R_3$ is a 5-membered heteroaryl radical that contains 1N, O or S atom as hetero atom and said heteroaryl is unsubstituted or is substituted by at least one of unsubstituted lower alkyl, fluorinated lower alkyl, lower alkoxy, halogen, unsubstituted amino, lower alkylated amino, and by free carboxy, lower alkoxycarbonyl, carbamoyl, N-lower alkylcarbamoyl, and N,N-di-lower alkylcarbamoyl; or $R_3$ is said 5-membered heteroaryl radical substituted by N-(benzenesulfonyl)-carbamoyl that is unsubstituted or is substituted by at least one of lower alkyl, lower alkoxy, and halogen; $R_4$ is free carboxy, lower alkoxycarbonyl, carbamoyl, N-lower alkylcarbamoyl, N,N-di-lower alkylcarbamoyl, or 5-tetrazolyl; or $R_4$ is N-(benzenesulfonyl)-carbamoyl that is unsubstituted of is substituted in the phenyl moiety by at least one of lower alkyl, lower alkoxy, halogen and trifluoromethyl; and $R_5$ is hydrogen or lower alkyl; or a salt thereof.

2. A compound according to claim 1, of formula I, in which $R_1$ is lower alkyl or mono-, di- or poly-fluoro-lower alkyl, $R_2$ is hydrogen, lower alkyl, lower alkenyl or mono-, di- or poly-fluoro-lower alkyl, X is lower alkylene, oxy or thio, alk is lower alkylene, $R_3$ is pyrryl, thienyl or furyl each of which is unsubstituted or is substituted by at least one lower alkyl, lower alkoxy, halogen, carboxy, lower alkoxycarbonyl, amino, N-mono- or N,N-di-lower alkylamino, carbamoyl, N-mono- or N,N-di-lower alkylcarbamoyl and trifluoromethyl, $R_4$ is carboxy, lower alkoxycarbonyl, 5-tetrazolyl, carbamoyl, N-mono- or N,N-di-lower alkylcarbamoyl, or N-(benzenesulfonyl)-carbamoyl that is unsubstituted or substituted in the phenyl moiety by at least one of lower alkyl, lower alkoxy, halogen and trifluoromethyl, and $R_5$ is hydrogen or lower alkyl, or a salt thereof.

3. A compound according to claim 1 or 2 in which $R_1$ is lower alkyl, or a salt thereof.

4. A compound according to claim 1, of formula I, in which $R_1$ is $C_1$-$C_4$alkyl or $\omega,\omega,\omega$-trifluoro-$C_1$-$C_4$alkyl, $R_2$ is hydrogen, $C_1$-$C_4$alkyl, $C_2$-$C_4$alkenyl or $\omega,\omega,\omega$-trifluoro-$C_1$-$C_4$alkyl, X is $C_1$-$C_3$alkylene, oxy or thio, alk is straight-chain $C_2$-$C_6$alkylene, n is 1 or 2, $R_3$ is pyrryl, thienyl or furyl, each of which is unsubstituted or is substituted by at least one of $C_1$-$C_4$alkyl, $C_1$-$C_4$alkoxy, halogen having an atomic number of up to and including 35, trifluoro-methyl, carboxy and $C_1$-$C_4$alkoxycarbonyl, $R_4$ is carboxy or N-(benzenesulfonyl)-carbamoyl, and $R_5$ is hydrogen, or a salt thereof.

5. A compound according to claim 1, of the formula in which $R_1$ is $C_1$-$C_4$alkyl, $R_2$ is $C_1$-$C_4$alkyl, X is oxy, alk is $C_2$-$C_6$alkylene, n is 1 or 2, $R_3$ is pyrryl, thienyl or furyl, each of which is unsubstituted or is substituted by $C_1$-$C_4$alkyl, $C_1$-$C_4$alkoxy, halogen having an atomic number of up to and including 35, trifluoromethyl or by $C_1$-$C_4$alkoxycarbonyl, $R_4$ is carboxy, and $R_5$ is hydrogen, or a salt thereof.

6. A compound according to claim 1, of the formula

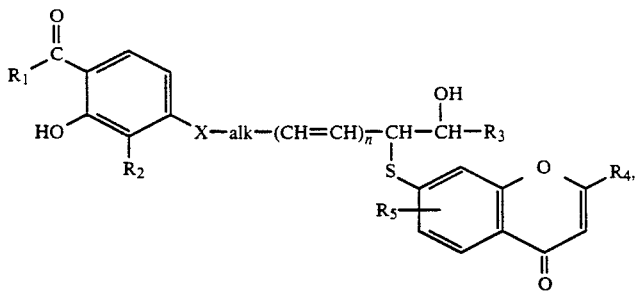

in which $R_1$ is $C_1$–$C_4$alkyl, $R_2$ is $C_1$–$C_4$alkyl, X is oxy, alk is $C_2$–$C_6$alkylene, n is 2, $R_3$ is thienyl or furyl, each of which is unsubstituted or is mono- or di-substituted by at least one of $C_1$–$C_4$alkyl, $C_1$–$C_4$alkoxy, halogen having an atomic number of up to and including 35 and trifluoromethyl, $R_4$ is carboxy, and $R_5$ is hydrogen, or a salt thereof.

7. A compound according to claim 1, of the formula

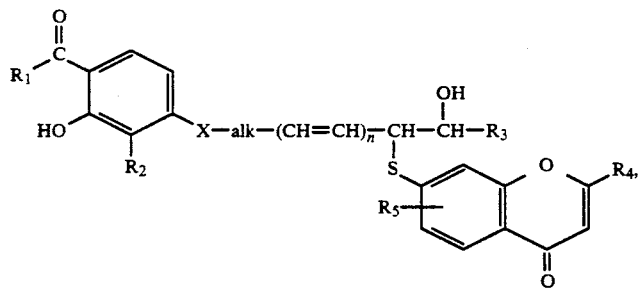

in which $R_1$ is $C_1$–$C_4$alkyl, $R_2$ is $C_1$–$C_4$alkyl, X is oxy, alk is $C_2$–$C_5$alkylene, n is 2, $R_3$ is 3-thienyl or 3-furyl each of which is unsubstituted or is mono- or di-substituted by halogen having an atomic number of up to and including 35, $R_4$ is carboxy and $R_5$ is hydrogen, or a salt thereof.

8. A compound according to claim 1, in which the double bond joined to the radical alk is in the (Z)-, that is the cis-configuration, and the additional double bond that may be present is in the (E)-, that is the trans-configuration.

9. A compound according to claim 1, in which the chain carbon atom bonded to the sulfur atom has the (S)-configuration and the chain carbon atom carrying the hydroxy group has the (R)-configuration.

10. A compound according to claim 1 being 7-[(1RS,2SR)-1-hydroxy-1-(thiophen-3-yl)-10-(4-acetyl-3-hydroxy-2-propyl-phenoxy)-deca-3(E),5(Z)-dien-2-ylthio]-4-oxo-4H-1-benzopyrane-2-carboxylic acid methyl ester.

11. A compound according to claim 1 being 7-[(1RS,2SR)-1-hydroxy-1-(thiophen-3-yl)-10-(4-acetyl-3-hydroxy-2-propyl-phenoxy)-deca-3(E),5(Z)-dien-2-ylthio]-4-oxo-4H-1-benzopyrane-2-carboxylic acid or a salt thereof.

12. A compound according to claim 1 being 7-[1RS,2SR)-1-hydroxy-1-(thiophen-3-yl)-8-(4-acetyl-3-hydroxy-2-propylphenoxy)-octa-3(E),5(Z)-dien-2-ylthio]-4-oxo-4H-1-benzopyrane-2-carboxylic acid methyl ester.

13. A compound according to claim 1 being 7-[(1RS,2SR)-1-hydroxy-1-(thiophen-3-yl)-8-(4-acetyl-3-hydroxy-2-propylphenoxy)-octa-3(E),5(Z)-dien-2-ylthio]-4-oxo-4H-1-benzopyrane-2-carboxylic acid or a salt thereof.

14. A compound according to claim 1 being 7-[(1RS,2SR)-1-hydroxy-1-(fur-3-yl)-10-(4-acetyl-3-hydroxy-2-propylphenoxy)-deca-3(E),5(Z)-dien-2-ylthio]-4-oxo-4H-1-benzopyrane-2-carboxylic acid or a salt thereof.

15. A compound according to claim 1 being 7-[(1RS,2SR)-1-hydroxy-1-(fur-3-yl)-9-(4-acetyl-3-hydroxy-2-propylphenoxy)-nona-3(E),5(Z)-dien-2-ylthio]-4-oxo-4H-1-benzopyrane-2-carboxylic acid or a salt thereof.

16. A compound according to claim 1 being 7-[(1RS,2SR)-1-hydroxy-1-(fur-3-yl)-8-(4-acetyl-3-hydroxy-2-propylphenoxy)-octa-3(E),5(Z)-dien-2-ylthio]-4-oxo-4H-1-benzopyrane-2-carboxylic acid or a salt thereof.

17. A compound according to claim 1 being 7-[(1RS,2SR)-1-hydroxy-1-(2,5-dichlorothiophen-3-yl)-10-(4-acetyl-3-hydroxy-2-propylphenoxy)-deca-3(E),5(Z)-dien-2-ylthio]-4-oxo-4H-1-benzopyrane-2-carboxylic acid methyl ester.

18. A compound according to claim 1 being 7-[(1RS,2SR)-1-hydroxy-1-(2,5-dichlorothiophen-3-yl)-10-(4-acetyl-3-hydroxy-2-propyl-phenoxy)-deca-3(E),5(Z)-dien-2-ylthio]-4-oxo-4H-1-benzopyrane-2-carboxylic acid or a salt thereof.

19. A pharmaceutical composition for the treatment of an allergic disease comprising a therapeutically effective amount of a compound according to claim 1 in admixture with one or more conventional pharmaceutical carriers.

20. A method of treating an allergic disease in an animal in need thereof which comprises administering a therapeutically effective amount of a compound according to claim 1.

* * * * *

UNITED STATES PATENT AND TRADEMARK OFFICE
CERTIFICATE OF CORRECTION

PATENT NO. : 5,145,868
DATED : September 8, 1992
INVENTOR(S) : ANDREAS VON SPRECHER ET AL.

It is certified that error appears in the above-identified patent and that said Letters Patent is hereby corrected as shown below:

Column 24:

In claim 2, line 7, after "at least one" insert ---of---.

In claim 3, line 1, after "claim 1" delete "or 2".

In claim 4, line 37, after "carboxy and" insert --by--.

Signed and Sealed this

Twelfth Day of October, 1993

Attest:

BRUCE LEHMAN

*Attesting Officer*    *Commissioner of Patents and Trademarks*